United States Patent [19]
Van Stee

[11] 3,949,752
[45] Apr. 13, 1976

[54] MENSTRUAL DEVICE FOR AN ANIMAL

[76] Inventor: Beverly Van Stee, 315 Yorktown Drive, Chapel Hill, N.C. 27514

[22] Filed: Aug. 31, 1973

[21] Appl. No.: 393,320

[52] U.S. Cl. .................................. 128/270; 128/285
[51] Int. Cl.² .......................................... G61F 13/20
[58] Field of Search .......................... 128/270, 285

[56] References Cited
UNITED STATES PATENTS

| | | |
|---|---|---|
| 1,575,123 | 3/1926 | Martocci-Pisculli ............... 128/270 |
| 1,582,201 | 4/1926 | Whittaker .......................... 128/270 |
| 1,669,295 | 5/1928 | Hallenberg ........................ 128/270 |
| 2,587,515 | 2/1952 | Parish ............................... 128/285 |
| 3,490,454 | 1/1970 | Goldfarb et al. ................... 128/285 |
| 3,528,419 | 9/1970 | Joechle ............................. 128/270 |
| 3,639,562 | 2/1972 | Gordon et al. .................... 128/270 |

FOREIGN PATENTS OR APPLICATIONS

| | | |
|---|---|---|
| 550,638 | 1/1943 | United Kingdom ................ 128/270 |
| 487,402 | 12/1929 | Germany ........................... 128/270 |
| 2,848 | 2/1907 | United Kingdom ................ 128/270 |

Primary Examiner—Aldrich F. Medbery
Attorney, Agent, or Firm—Cennamo Kremblas & Foster

[57] ABSTRACT

A menstrual device for an animal — particularly a canine bitch — of the tampon and depositor type. The absorbent tampon is extremely small in comparison to human type and varies in size in dependence on the size of the animal. The composition of the tampon is especially characterized by including a deodorizer and a spermicidal agent to prevent pregnancy. The tampon additonally includes a lubricant rearwardly for ease of removal.

6 Claims, 3 Drawing Figures

MENSTRUAL DEVICE FOR AN ANIMAL

BACKGROUND

The prior art is replete with menstrual devices of the occulsive, intravaginal collecting type for the menstrual debris. All of these products, however, are intended for human use; and primarily due to the anatomy — particularly the canine bitch — their use can not be extended to the animal.

The heat cycle of a mature canine bitch is known to occur twice a year each for periods of ten to fourteen days. During this time of ovulation the proestrous and estrous bitch secretes first a sanguineous discharge and later a seromucous discharge. These discharges are attractive to male animals and facilitate successful copulation. The objectional nuisance and soiling are well understood without expounding. Additionally missmating or undesireable mating can and does occur.

A search of the prior art does not reveal an intravaginal menstrual tampon for a canine bitch. Further, an attempted use of a human type of tampon in an animal may prove to be extremely dangerous to the life of the animal. The physical anatomical structure of the animal's canal is distinct. Having knowledge of the anatomy of the animal a conventional type of tampon with lubricant may be inserted in the vaginal canal; however, its removal is almost impossible and may lead to the destruction of the vaginal canal of the animal.

SUMMARY OF THE INVENTION

The present invention relates to a menstrual tampon intended for animal use. The actual structure overall is small in comparison to the standard types of human tampon — and may vary in size in accordance with the size of the animal. The structure further comprises a string, and a lubricant seal at the extreme rearwardly end of the tampon for ease of removal. The composition includes in addition to the absorbent guaze a deodorizer and a spermicidal agent.

In use the tampon includes the customary tube and rod and upon insertion in the animal vaginal canal the tampon is directed upwardly and then horizontally into position. The removal with the assistance of the lubricant is a straight pull on the string.

OBJECTS

It is accordingly a principal object of the present invention to provide a tampon to collect the menstrual fluids of an animal.

Another object is to provide such a tampon that may be used by the general public without the danger of the tampon being permanently placed.

A further object of the invention is to provide a composition for an animal tampon that eliminates the customary odors and conception.

Other objects and features of the present invention will become apparent from the following detailed description when taken in conjunction with the drawings in which:

DETAILED DESCRIPTION OF DRAWINGS

Figure 1:
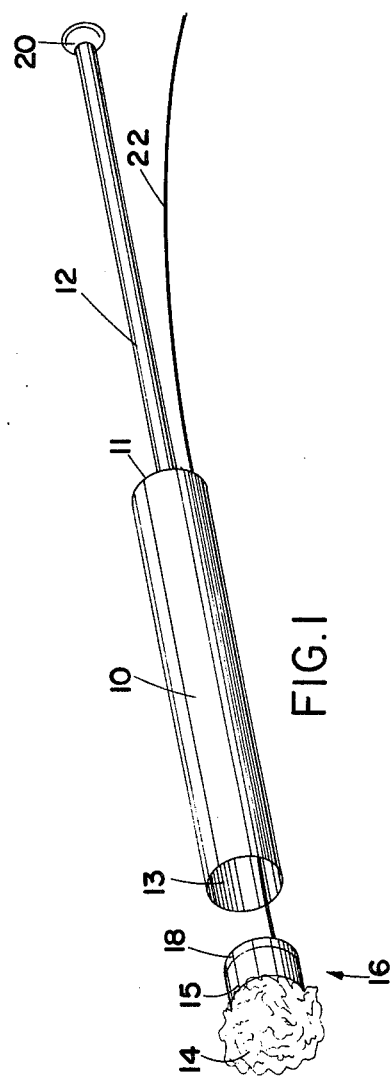
FIG. 1 is an overall view of the preferred embodiment of the present invention.
Figure 2:
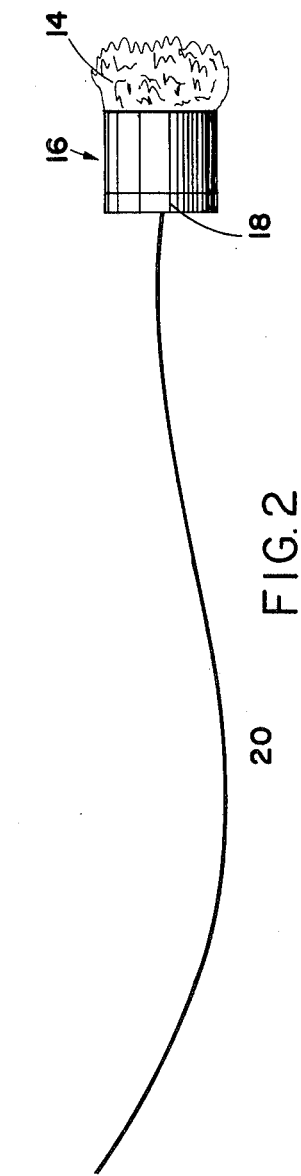
FIG. 2 is an enlarged view of the tampon per se of the preferred embodiment of the invention.

With particular reference now to FIGS. 1 and 2 there is shown the preferred embodiment of the invention. The outwardly structure appears much the same as the conventional human tampon except for its smaller size. There are distinct structural differences as hereinafter described, that make the tampon of the preferred embodiment particularly adaptable for use with animals.

A semi-rigid tubular member 10 has opposing open ends 11 and 13 — commonly referred to as the applicator. The tampon 16 may be of a various composition such as gauze, compressed cotton, or synthetic absorbent material. The tampon 16 is positioned in the open end 13 of the applicator 10 and the slidable ejector 12 enters the opposite end 11 of the applicator 10. All much similar to the conventional tampon and applicator.

The tampon 16, per se, comprises three primary parts, the absorbent body 14, the enclosure 15, and the lubricant seal 18. With particular reference now to FIG. 2 the enclosure, lubricant, body, and pull string are illustrated more clearly. The string 20 is knotted at its extreme end — on the inside of enclosure 16. In this way a pull on the string will retrieve the overall assembly. At the most rearwardly end of the enclosure 16 (opposite the absorbent 14) is the end that comprises the lubricant seal 18. In operation the interaction of body fluid and encapsulating material results in a dissolving of the sealed lubricant, and thereby releasing the lubricant in advance of the tampon being removed (by pull on string 20) from the animal vaginal canal.

In the preferred embodiment the lubricant is sealed into a congealed mass by normal ambient air temperature to prevent its absorbtion by the tampon — since the sole purpose of the lubricant is to facilitate removal. Of course, other equivalent means may be utilized to release the lubricant upon withdrawing the tampon.

The primary chemical ingredient of the lubricant in this embodiment is carbowax — a waxy semi-solid substance having a melting point at the body temperature of the animal. Also the melted lubricating fluid contains a spermicidal agent which tends to reduce — if not eliminate — the likelihood of conception and pregnancy; and in this embodiment nonoxynol.

The absorbent material 14 in fabrication is saturated with a deodorant to eliminate the customary odors. The chemical deodorant may be benzethonium chloride. This deodorizer tends to reduce the attractiveness of the bitch to males.

The applicator is so constructed for ease of insertion in the vaginal canal. The construction and shape of tampon applicators are well understood in the art. The presence of physiological secretions should be a sufficient lubricant for insertion of the tampon. However, if with certain animals additional insertion lubricant on the front end of the tampon would be required, the prior art teaches the same.

Figure 3:
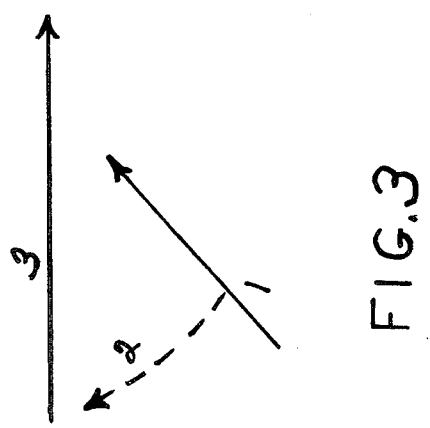
FIG. 3 illustrates, graphically, the sequential directions of insertion of the tampon into the vaginal canal of a canine bitch.

In using the tampon of the present invention — with reference to FIG. 3, the end of the applicator with the insertion configuration — opposite to that with the string extending — is inserted into the vestibule of the vaginal canal and pushed in the vagina in an upwardly direction for approximately an inch to the cul-de-sac.

When the cul-de-sac is passed the applicator 16 is advanced horizontally until it stops. The plunger 12 is pushed and the applicator withdrawn leaving the tampon in place. The string 22 hangs for an inch or two externally for removal of the tampon.

When it is desired to remove the tampon the string is pulled. The continued pull force then reacts on the tampon causing it to withdraw following the lubricant which has been released at the rear end of the tampon by the body temperature of the vagina melting the semi-solid carbowax.

Although a single preferred embodiment is shown and described modifications may be had without departing from the scope of the invention.

I claim:

1. A tampon for use with a lower animal having an angular vaginal canal with a cul-de-sac comprising an enclosure having a menstrual fluid absorbent material on a forward end and a means to permit easy removal including a lubricant means on the rear end having a means for releasing the lubricant after insertion to provide a lubricated return path for the tampon.

2. The tampon of claim 1 wherein said lubricant releasing means comprises a string also attached to said tampon.

3. The tampon of claim 1 wherein said absorbent material further comprises a deodorant.

4. The tampon of claim 1 wherein said lubricant material further comprises a spermicide.

5. The tampon of claim 1 wherein said lubricant is a carbowax.

6. The method of utilizing a tampon for the capture of menstrual fluids of a lower animal having a non-linear vaginal canal with a cul-de-sac comprising the steps of providing a tampon with an absorbent body enclosure and holding means on one end and a lubrication dispensing means on the other end, placing the tampon in the vagina vestibule with the absorbent body facing forwardly and inwardly and the dispensing means facing rearwardly, inserting the tampon in the vaginal canal upwardly a short distance, then continuing the insertion horizontally the required distance, leaving the tampon in place a suitable time to permit release of the lubricant from the dispensing means and to capture of menstrual fluids, and then removing the tampon rearwardly as the dispensing means provides lubrication for the outward passage through the angular vaginal canal.

* * * * *